(12) United States Patent
Piechnik et al.

(10) Patent No.: US 9,285,446 B2
(45) Date of Patent: Mar. 15, 2016

(54) SYSTEMS AND METHODS FOR SHORTENED LOOK LOCKER INVERSION RECOVERY (SH-MOLLI) CARDIAC GATED MAPPING OF T1

(75) Inventors: Stefan K. Piechnik, Oxford (GB); Matthew D. Robson, Oxford (GB); Andreas Greiser, Erlangen (DE)

(73) Assignee: Isis Innovation Limited, Oxford (GB)

( * ) Notice: Subject to any disclaimer, the term of this patent is extended or adjusted under 35 U.S.C. 154(b) by 1190 days.

(21) Appl. No.: 13/248,533

(22) Filed: Sep. 29, 2011

(65) Prior Publication Data

US 2012/0078084 A1    Mar. 29, 2012

Related U.S. Application Data

(60) Provisional application No. 61/387,591, filed on Sep. 29, 2010.

(51) Int. Cl.
*G01R 33/50* (2006.01)
*A61B 5/055* (2006.01)

(52) U.S. Cl.
CPC ........ *G01R 33/50* (2013.01); *A61B 5/055* (2013.01)

(58) Field of Classification Search
CPC .................................. G01R 33/50; A61B 5/055
USPC ............................................................ 600/413
See application file for complete search history.

(56) References Cited

PUBLICATIONS

Messrogphli et al., Optimization and Validation of a Fully-Integrated Pulse Sequence for Modified Look-Locker Inversion-Recovery (MOLLI) T1 Mapping of the Heart, Journal of Magnetic Resonance Imaging 26:1081-1086, 2007.*
Paul James Hilt, Thesis, Quantification of Cardiac Longitudinal Relaxation (T1) At 3.0 T During Normal and Hyperoxic Breathing Conditions, Aug. 2008.*
RMSSE, http://www.uta.edu/faculty/sawasthi/Statistics/glosr.html, Nov. 2007.*

* cited by examiner

*Primary Examiner* — Bo J Peng
(74) *Attorney, Agent, or Firm* — Thomas | Horstemeyer, LLP

(57) ABSTRACT

A shortened version of the MOLLI sequence (Sh-MOLLI) is described which generates rapid and high-resolution myocardial spin-lattice (T1) maps. The Sh-MOLLI technique is based on a significant abbreviation of pre-existing TI sampling scheme combined with the use of processing logic to bypass the major side effects of the above sampling scheme abbreviation and distinguish between long and short T1 relaxation times in order to conditionally utilize available TI samples for non-linear T1 fitting.

25 Claims, 12 Drawing Sheets
(6 of 12 Drawing Sheet(s) Filed in Color)

SYSTEMS AND METHODS FOR SHORTENED LOOK LOCKER INVERSION RECOVERY (SH-MOLLI) CARDIAC GATED MAPPING OF T1

CROSS-REFERENCE TO RELATED APPLICATION

This application claims priority to, and the benefit of, U.S. Provisional Patent Application entitled, "SYSTEMS AND METHODS FOR SHORTENED LOOK LOCKER INVERSION RECOVERY (Sh-MOLLI) CARDIAC GATED MAPPING OF T1," having Ser. No. 61/387,591, filed on Sep. 29, 2010, which is incorporated by reference in its entirety.

TECHNICAL FIELD

The present disclosure generally relates to medical imaging and more particularly, relates to systems and methods for performing shortened modified Look Locker inversion recovery (Sh-MOLLI) cardiac gated mapping of T1.

BACKGROUND

In magnetic resonance (MR) imaging, tissue contrast is generated by a combination of intrinsic tissue properties such as spin-lattice (T1) and spin-spin (T2) relaxation times, and extrinsic properties such as imaging strategies and settings. Signal intensity in conventional MR images is displayed on an arbitrary scale, and thus is not adequate for direct comparisons. A major advantage of myocardial T1-mapping is absolute quantification of structural changes that is largely independent of imaging parameters, thereby allowing for objective comparisons between examinations. T1-relaxation times depend on the composition of tissues. T1-relaxation times exhibit characteristic ranges of normal values at a selected magnetic field strength. Deviation from established ranges can thus be used to quantify the effects of pathological processes. Focal and global T1 changes are reported in a number of myocardial diseases, such as myocardial infarction, heart failure, valvular heart disease, and systemic diseases with cardiac involvement such as amyloidosis and systemic lupus erythematosus.

T1-mapping may be a sensitive technique for detecting diffuse fibrosis in heart failure and valvular heart disease, which have been described by abnormal post-contrast T1 values but not by conventional late gadolinium enhanced (LGE) imaging. One method for performing myocardial T1-mapping is the modified Look Locker inversion recovery (MOLLI) pulse sequence. With reference to FIG. 1, MOLLI merges images from three consecutive inversion-recovery (IR) experiments into one data set, generating single-slice T1 maps of the myocardium. The MOLLI technique involves relatively long recovery epochs, prolonging measurement time. One perceived shortcoming with the MOLLI technique is the long 17 heart beat breath-hold required to perform MOLLI. Such a long period may be challenging for many cardiac patients whose heart rate is slowed by betablocker therapy as well as for patients who suffer from breathlessness, especially older subjects. Accordingly, there is a need to address the aforementioned deficiencies and inadequacies.

SUMMARY

Briefly described, one embodiment, among others, is a method for performing myocardial spin-lattice (T1) mapping. The method comprises performing consecutive inversion-recovery (IR) experiments that include front-loaded sampling followed by one or more subsequent samples and conditionally including the subsequent one or more samples for the T1 mapping based on empirical relationships between the estimated spin-lattice relaxation time T1, heart rate, heart beat period or experimentally achieved relaxation recovery times or degrees, and estimated fit error associated with the subsequent experiments and samples.

Another embodiment is a method for performing myocardial spin-lattice (T1) mapping that comprises performing consecutive inversion-recovery (IR) experiments, wherein the consecutive IR experiments comprise a first IR experiment, a second IR experiment, and a third IR experiment, the first IR experiment comprising a number of samples exceeding a number of samples of both the second IR experiment and the third IR experiment. The method further comprises conditionally processing the samples in the first, second, and third IR experiments.

Another embodiment is a system comprising at least one computing device and at least one application executable in the at least one computing device, the at least one application comprising logic that performs consecutive inversion-recovery (IR) experiments comprising a first, second, and third IR experiment, wherein the IR experiments have a corresponding number of samples, and wherein the first IR experiment is front-loaded relative to the second and third IR experiments. The at least one application further comprises logic that conditionally utilizes spin-lattice (T1) samples in the first, second, and third IR experiments for non-linear T1 fitting based on T1 relaxation times.

Other systems, methods, features, and advantages of the present disclosure for performing myocardial T1-mapping will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
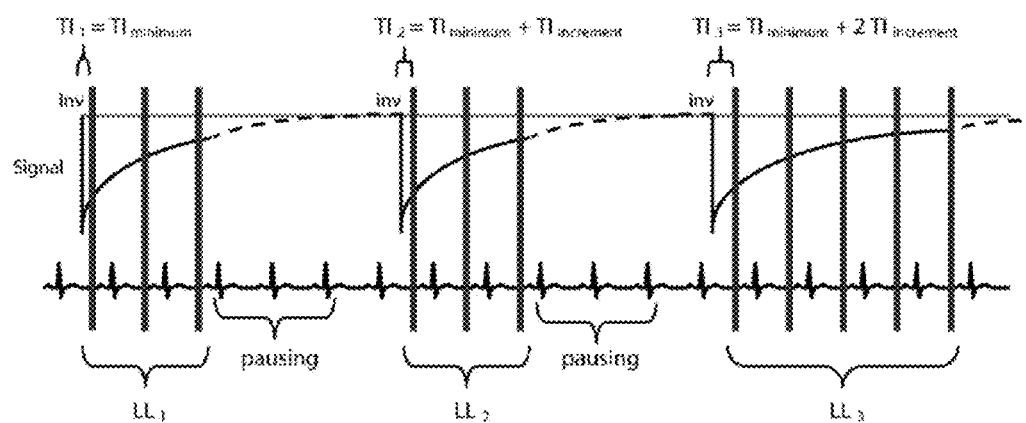
FIG. 1 depicts the MOLLI technique where images from three consecutive inversion-recovery (IR) experiments are merged into one data set, thereby generating single-slice T1 maps of the myocardium.

Having summarized various aspects of the present disclosure, reference will now be made in detail to the description of the disclosure as illustrated in the drawings. While the disclosure will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

Quantitative mapping of spin-lattice (T1) relaxation time use repeated inversion recovery (IR) experiments with very short recovery periods that impact subsequent measurements depending on measured T1. Known approaches such as modified Look Locker inversion recovery (MOLLI) require relatively long recovery epochs, thereby prolonging the measurement time and progressively increasing the estimation errors for the long T1 relaxation times or fast heart rates.

Various embodiments of a shortened version of the MOLLI sequence (Sh-MOLLI) are described herein which generate rapid and high-resolution myocardial spin-lattice (T1) maps without the use of contrast agents in a single short breath-hold involving less heartbeats than required for a MOLLI sequence. For some implementations, the shortened modified Look Locker inversion recovery (Sh-MOLLI) technique is performed in twelve heartbeats or less. Various embodiments of the Sh-MOLLI technique are based on an abbreviated TI sampling scheme combined with the use of processing logic to distinguish between long and short T1 relaxation times in order to conditionally utilize available TI samples for non-linear T1 fitting.

One embodiment is a method for performing myocardial T1 mapping. The method comprises performing consecutive inversion-recovery (IR) experiments that include front-loaded sampling followed by one or more subsequent experiments yielding a set of additional samples. The method further comprises conditionally including the subsequent one or more samples for the T1-mapping based on several concurrent estimates of T1 recovery time and respective fit errors associated with the subsequent samples.

In a further embodiment, T1 values that are larger than a predetermined interval (e.g., the heartbeat interval) are considered adequately estimated using just a single inversion recovery (IR) experiment. Additional IR experiments are used typically only to estimate short T1 values based on the respective estimates and the measures of additional improvement in the recovery curve. Thus, in an embodiment of the present Sh-MOLLI technique, minimal recovery times are combined with conditional data reconstruction. In one embodiment, the conditional data reconstruction is conducted algorithmically based on certain conditions, equivalent to using binary weighting of input parameters. In another embodiment, the conditional data processing is achieved using weighted processing, for example using weights from a continuous scale.

Multiple datasets including a front-loaded data set are utilized based on original data to determine the inclusion of potentially suboptimal data samples. In accordance with such embodiments, progressive fitting of linear or non-linear models for these data sets are used to identify and reject samples identified as being suboptimal from available measurements. As described below, a first embodiment is directed to binary weighting of input parameters in model identification. While some embodiments incorporate binary weighting of input parameters in model identification, alternative embodiments incorporate weighting on a continuous scale whereby all samples are used.

In one embodiment of a Sh-MOLLI sequence, a first front-loaded group of samples with presumed optimal parameters is collected and fitted. Based on the results obtained from the first group of samples, additional samples and non-linear fitting may or may not be performed to improve accuracy over an extended range of parameters. Conditional data processing is performed and additional solutions are accepted when solutions fall within predetermined limits. Specifically, for some embodiments, additional solutions are accepted if the new solution is characterized by improved fit quality. Furthermore, a limit is placed on the processing time where further solutions are not sought when previous steps indicate that they are not necessary.

Figure 2A:
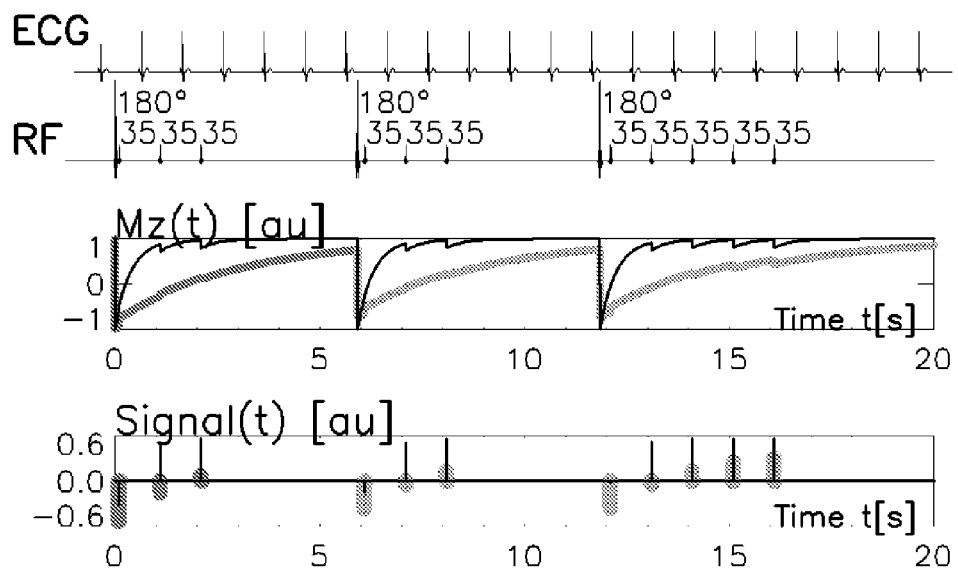
FIGS. 2A-B show a side-by-side simulated comparison of ECG-gated pulse sequence schemes for simulation of a) MOLLI and b) Sh-MOLLI at a heart rate of 60 bpm.
Figure 2B:
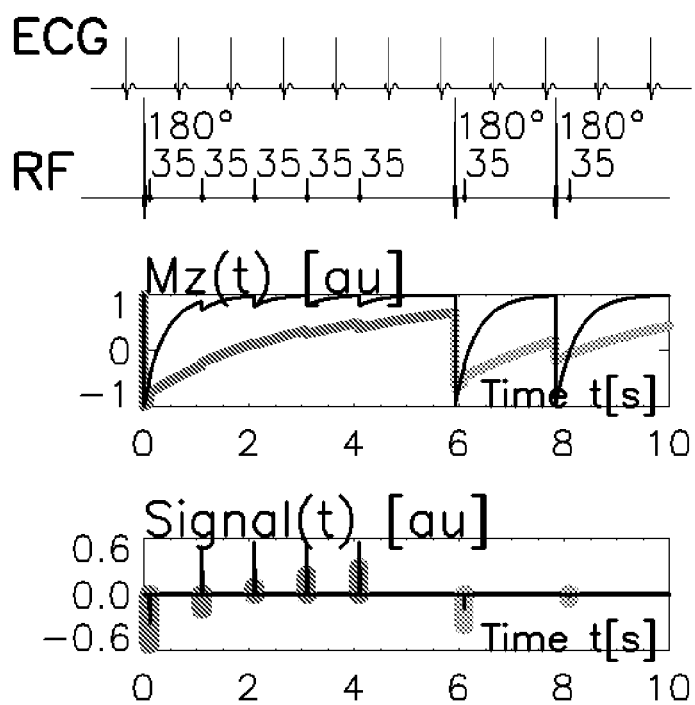

Reference is made to FIGS. 2A-2B, which show a side-by-side simulated comparison of ECG-gated pulse sequence schemes for simulation of a) MOLLI and b) Sh-MOLLI at a heart rate of 60 bpm. Steady-state free precession (SSFP) readouts are simplified to a single 35° pulse each, presented at a constant delay time TD from each preceding R wave. The 180° inversion pulses are shifted depending on the IR number to achieve the desired shortest TI (which may be but are not limited to such values as 100, 180 and 260 ms) in the consecutive inversion recovery (IR) experiments.

The plots shown in FIGS. 2A-B represent the evolution of longitudinal magnetization (Mz) for short T1 (400 ms, thin traces) and long T1 (2000 ms, thick lines). Note that long epochs free of signal acquisitions minimize the impact of incomplete Mz recoveries in MOLLI so that all acquired samples can be pooled together for T1 reconstruction. For Sh-MOLLI, the validity of additional signal samples from the 2nd and 3rd IR epochs is determined on-the-fly by progressive non-linear estimation so they can be used when deemed necessary or rejected when invalid.

Simulations were performed in IDL (Interactive Data Language ver. 6.1, ITT Visual Information Solutions) by implementing equations for the piece-wise calculation of longitudinal magnetization ($Mz(t)$) and the signal samples generated by a train of arbitrarily-spaced ideal excitation pulses. Inversion pulses were assumed to be perfect 180° excitations, and readout pulses were 35°. Both sequences had three IR epochs.

Simulations were performed for MOLLI based on its optimized variant, which collects 3+3+5 samples in three consecutive IR epochs separated by long recovery periods (FIG. 2A).

As shown in FIG. 2B, with the Sh-MOLLI technique, 5+1+1 samples were collected in less than 10 heartbeats. It should be emphasized that the 5+1+1 sequence here is just one of various possible sequences that may utilized for Sh-MOLLI, and other sequence schemes may be implemented. IR epochs were separated by only one TRR (R-R interval). Abbreviated Sh-MOLLI recovery epochs mean that Mz can be severely affected by preceding IR epochs in the Sh-MOLLI sequence (FIG. 2B) so that the signal samples from the 2nd and 3rd IR obtained using Sh-MOLLI do not fit the IR equations as outlined for MOLLI. This problem is circumvented by conditional data analysis according to the algorithm described in more detail below.

For this example, given an adequate signal level, non-linear identification of T1 is always performed for samples 1-5 (S1-5) from the 1st IR, with samples from the 2nd (S6) and 3rd (S7) IR being used only if the estimated T1 values are short (<TRR) or very short (<0.4 TRR), respectively. Thus, in this embodiment, use of sample datasets S1-6) are accepted only if estimated T1 falls below a heart beat interval (TRR), and use of sample datasets S1-7 are accepted only if estimated T1 falls below 0.4 TRR. The final T1 is accepted only if the quality of fit sufficiently improves in comparison to the TRR. Simulations using both sequences outlined in FIGS. 2A-B were performed for T1 ranging from 50 to 2700 ms (50 ms increments) and for heart rate (HR) between 40-100 bpm (20 bpm increments) and adding noise representative of measurement conditions.

Having described the basic framework, details for implementing Sh-MOLLI are now described, which combines minimal recovery times with conditional data reconstruction. Embodiments of Sh-MOLLI may be implemented as 2, 3, or more inversion-recovery (IR) experiments split over a predetermined number of heartbeats to collect SSFP images with varying TI, typically on the order of 100-5000 ms, whereby the first IR experiment is "front-loaded" with more pulses. Conditional data processing is then performed to determine whether subsequent samples are to be included and with what impact they may have on the final estimate.

Figure 3:
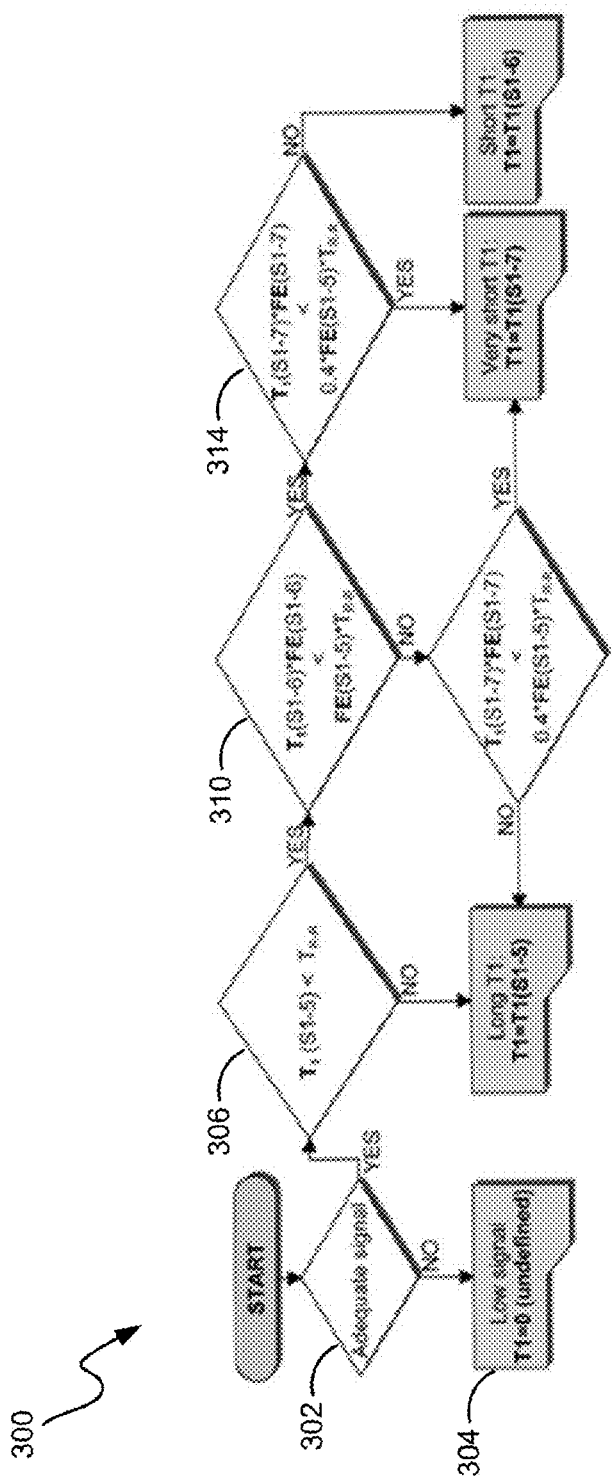
FIG. 3 is a flowchart for performing conditional data processing to establish appropriate processing sequence for example "long," "short," and "very short" T1 categories.

Reference is made to FIG. 3, which is a flowchart 300 for performing one embodiment of the conditional data processing. An algorithm is implemented for the inclusion of samples to circumvent the impact of suboptimally-short recovery epochs in T1 estimation. The fit error (FE) is calculated as the square root of the sum of squared residuals divided by number of samples minus one. "S1-5" denotes the set of samples from the first inversion recovery. "S1-6" and "S1-7" denote the set of samples from the first inversion recovery supplemented by samples from consecutive IR experiments. $T_{R-R}$ is a heart beat interval.

Note that while the first data set comprises 5 pulses followed by 1+1 pulses for this non-limiting example, the data sets are not limited to these numbers and other front-loaded schemes (e.g., 5+2+1, 5+1 +2) may be implemented. In some embodiments, a front-loaded scheme can be implemented in which the number of samples from the first experiment exceeds the number of samples from a subsequent experiment. In other embodiments, a front-loaded scheme can be implemented in which the number of samples from the first experiment exceeds the number of samples from all subsequent experiments. Samples are obtained with potentially suboptimally short recovery periods due to repeated Look-Locker Inversion recovery experiments (Sh-MOLLI) contained within a single breathhold. The fit error (FE) described above may also be replaced by another numerical representation of the empirical data consistency.

In accordance with one embodiment, conditional data processing is performed and Sh-MOLLI samples from the second and third IR are taken into account only if: 1) the estimated T1 is shorter than the R-R interval; and 2) if the second and third IR experiments improve non-linear fit. In the non-limiting example shown, a specific sampling method involving 5+1+1 samples in three IR experiments is used, separated by single recovery epochs.

In decision block 302, if an adequate signal is not present, then a low signal exists and processing stops (block 304). A predefined threshold may be used for this determination. An initial fit is performed using the first 5 samples, resulting in a T1 (S1-5) estimate—the recovery time for the first 5 samples. Processing continues based on whether the estimated T1 time is long (meaning equal to or longer than a heart beat interval $T_{R-R}$) or short (meaning less than a heart beat interval) (decision blocks 306, 310, 314).

For some embodiments, subsequent fits are performed to improve accuracy for the short T1 samples, only if T1 (S1-5) is less than the RR-period, the time between heartbeats (decision block 306). That is, if the T1 time for the first 5 samples is relatively short, subsequent samples are considered. Finally, the sample datasets of S1-6 and S1-7 are accepted and performed only if the estimated T1 falls below $T_{R-R}$ and $0.4*T_{R-R}$ respectively. Furthermore, the fit error (FE) normalized by the number of samples must be lower than the FE based on the first 5 samples (decision blocks 310, 314). Thus, a determination is made on how well subsequent samples (samples 6 and 7 in the non-limiting example of FIG. 3) match the recovery curve. This is done to ensure that noise and interference is not introduced by the latter samples following the front-loaded samples. Conditional reconstruction of incomplete recovery periods ensures that T1-mapping with a level of accuracy comparable to that by the MOLLI technique can be achieved in a shorter heartbeat breath-hold.

Figures 4A, 4B:
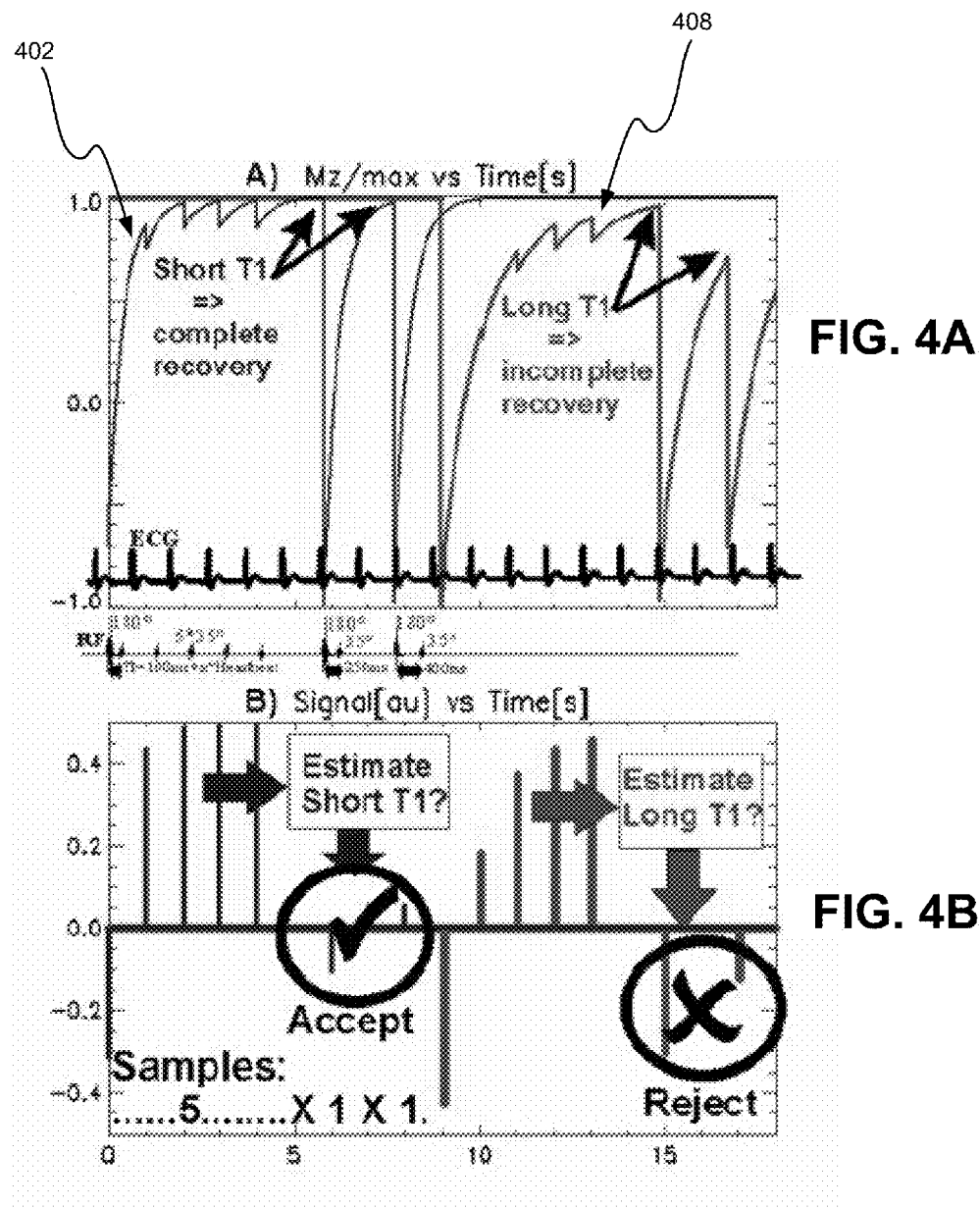
FIG. 4A illustrates the evolution of longitudinal magnetization during Sh-MOLLI acquisition for short and long T1.
FIG. 4B illustrates the concept of determination of validity of the additional signal samples performed on-the-fly.

Reference is made to FIGS. 4A-B. FIG. 4A illustrates the evolution of longitudinal magnetization during Sh-MOLLI acquisition for short 402 and long 408 T1 values. The long T1 408 is shown offset in time for clarity. The RF pulses in the inset are given for the short-T1 example. FIG. 4B illustrates an example of the determination of validity of the additional signal samples as appropriate for "very short" and the "long" T1 processing regimes.

One advantage of Sh-MOLLI is an approximately two-fold increase in speed of acquisition. The additional variation in T1-estimates is much less than the 25-50% expected from the reduced number of samples—likely due to the fact that Sh-MOLLI is less susceptible to movement artifacts accumulated within shorter breath-holds. Further underestimation of T1 values is only minor, especially when compared to the known bias of MOLLI, which is in the order of −5%.

Figure 5:
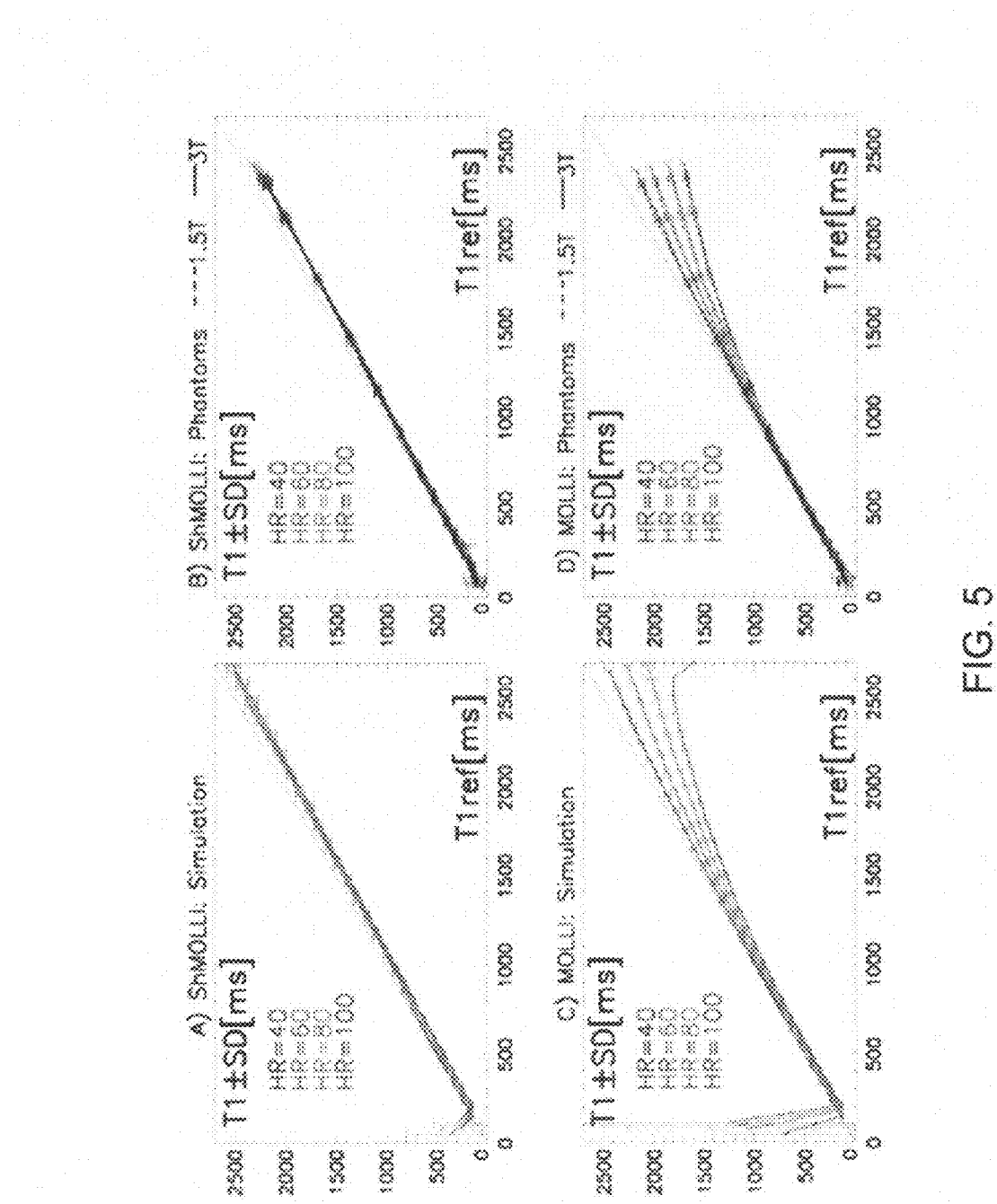
FIG. 5 illustrates the relationship between T1 in-silico simulations (left column panels) and in-vitro phantom measurements (right side panels) for Sh-MOLLI and MOLLI plotted against the corresponding reference (T1 ref) for a selection of simulated heart rates.

With reference to FIG. 5, results of simulations and phantom measurements show that the bias in Sh-MOLLI T1 estimates is relatively stable across a wide range of T1 values and independent of heart rate variation. As such, embodiments of Sh-MOLLI provide a fast, clinically applicable solution, which generates robust, quantitative single breath-hold T1 maps of the human myocardium with high resolution.

The accuracy of MOLLI and Sh-MOLLI is potentially dependent on both the T1 and heart rate (HR). For MOLLI, as HR and T1 increase, the T1 measurements diverge increasingly from the ideal identity line, as shown in FIG. 5. The Sh-MOLLI technique demonstrates reduction in these unwanted effects through a closer adherence to the diagonal identity line over extensive range of measured T1 values. Simulation (A&C) and Phantom (B&D) measurements in 3 T and 1.5 T (dashed lines) overlap and are in close agreement with simulation results. Note that the lines are offset by 15 ms horizontally for each HR value to reduce the overlap between lines.

Figure 6:
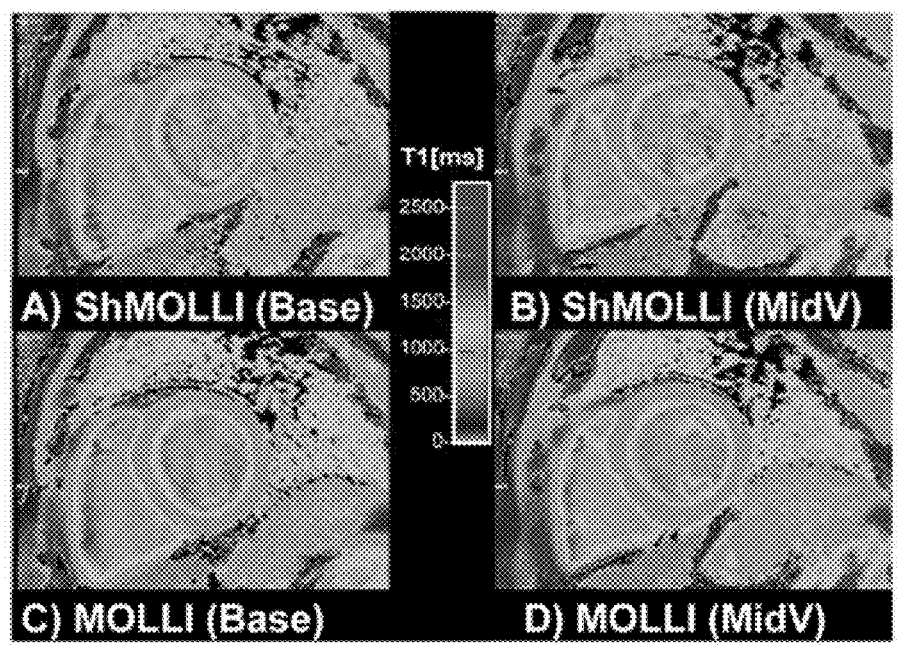
FIG. 6 is a representative basal and mid-ventricular (MidV) slice T1 maps of myocardium obtained using Sh-MOLLI and MOLLI at 1.5 T.
Figure 7:
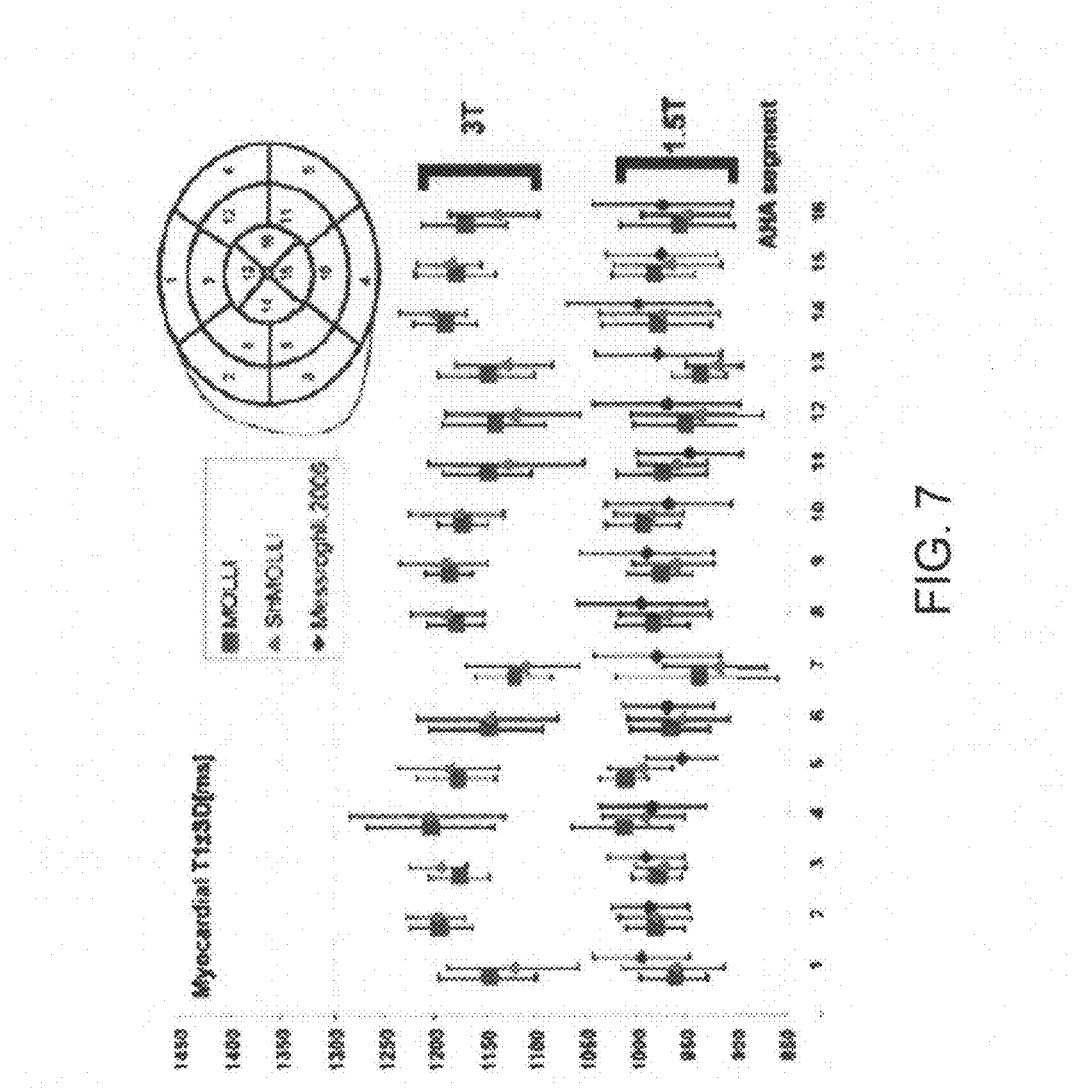
FIG. 7 shows T1 values for AHA myocardial segments 1-16 at 1.5 T and 3 T using Sh-MOLLI and MOLLI.
Figure 8:
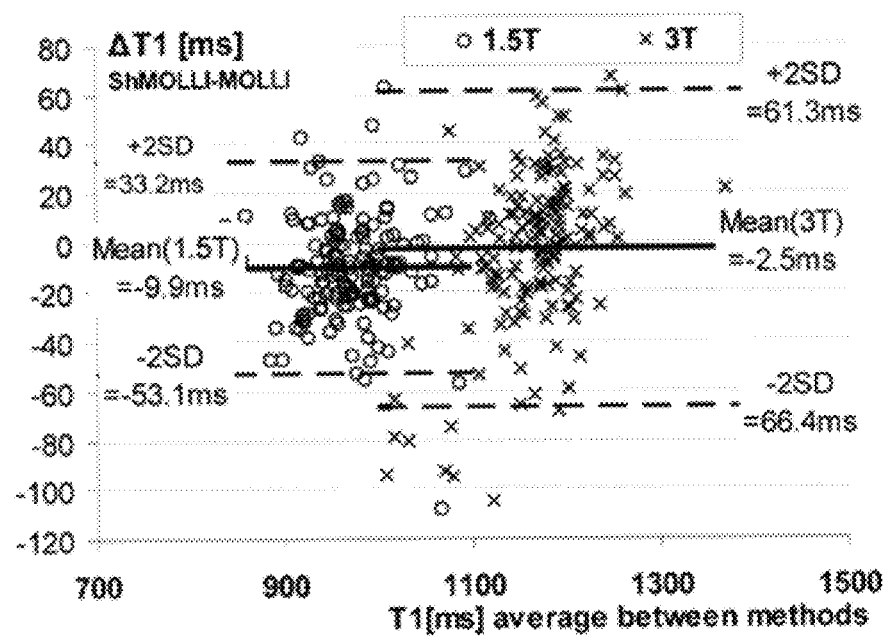
FIG. 8 is a Bland-Altman plot, which shows strong correlation between Sh-MOLLI and MOLLI myocardial T1 values at 1.5 T and 3 T.

FIG. 6 is a representative basal and mid-ventricular (MidV) slice T1 maps of myocardium obtained using Sh-MOLLI and MOLLI at 1.5 T. FIG. 7 shows T1 values for AHA myocardial segments 1-16 at 1.5 T and 3 T using Sh-MOLLI and MOLLI. FIG. 8 is a Bland-Altman plot, which shows a strong correlation between ShMOLLI and MOLLI myocardial T1 values at 1.5 T and 3 T at the normal heart rates of approximately 60 beats per minute. Compared to MOLLI, Sh-MOLLI underestimates myocardial T1 at 1.5 T (~1%), but there is no difference at 3 T. These relations may change in cases with increased heart rates, due to the recognized sensitivity of MOLLI estimates to shortening of the recovery times.

Figure 9:
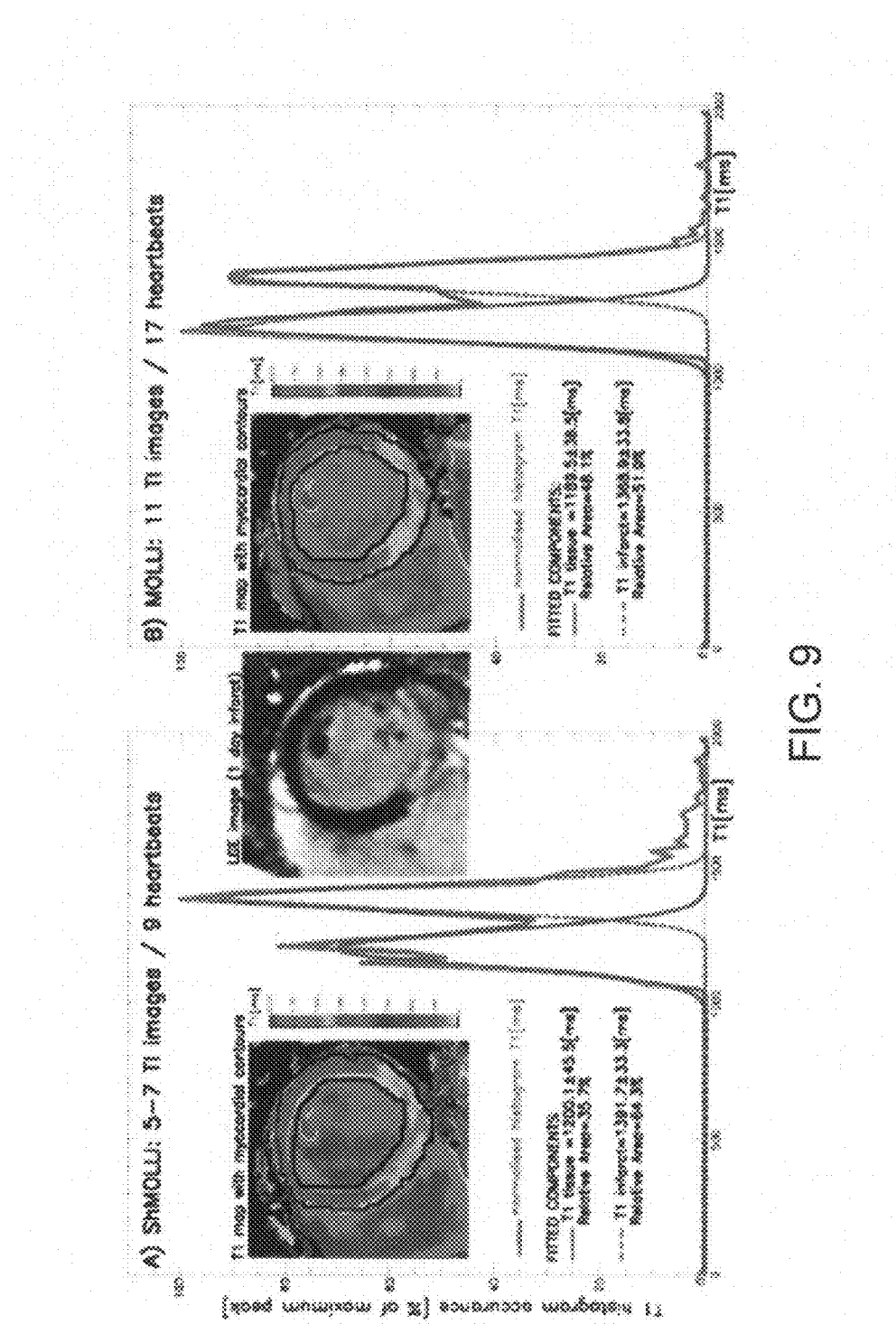
FIG. 9 shows the distribution of T1 in a patient with myocardial infarction at 3 T using A) Sh-MOLLI and B) MOLLI.

In a validation material, the distribution of differences is similar to the repetition accuracy at approximately ±16 ms (~1.6%) at 1.5 T and 29 ms (~2.4%) at 3 T. FIG. 9 shows the distribution of T1 in case #1 at 3 T using A) Sh-MOLLI and B) MOLLI. As shown, two distinct populations of values exist within the myocardium, which can be fitted using two Gaussian curves, corresponding to injured (long T1) and unaffected (normal T1) myocardium. Regions of increased T1 demonstrate remarkable spatial co-localization with LGE 4 days earlier (image insets).

It should be emphasized that there is a clear dependence of MOLLI errors on the heart rate (HR), with relative underestimation reaching −30% for the highest HR and longest T1 studied. In contrast, Sh-MOLLI calculations are not dependent on HR. For T1s longer than approximately 800 ms, the Sh-MOLLI error of underestimation is constant at −4%. This allows for easy correction of measured T1 errors in the range:

$$T1_{True} = \frac{T1_{Measured}}{1 + relativeError} \approx 1.04 \cdot T1_{Measured}$$

For shorter T1 values (<800 ms), this formula does not apply and estimation errors quickly change from negative to positive for both methods. The variability of T1 measurements across all simulations or pixels is shown as whiskers in FIG. 4. For long T1s, measurements by Sh-MOLLI are based on 5 rather than 11 pixel samples from images with different TI times as in MOLLI, with a predicted penalty of additional 48% increase in the variation of T1 measurements (noise penalty).

For shorter T1s, five or six TI samples are used with a predicted noise penalty of 35% and 25%, which is further complicated by heavily non-linear processing. In simulation studies, for the reference T1 range of 300-2600 ms, we find the average coefficient of variance (CV) is 2.7% for Sh-MOLLI and 2.1% for MOLLI (translating to an overall 28% noise penalty for using Sh-MOLLI). In phantom studies, the noise penalty for Sh-MOLLI is 21% at 3 T (FIG. 4B) and 61% at 1.5 T (FIG. 4 C).

Typically, the penalty for reducing the number of images collected for T1 reconstruction is increased noise or variability within the resulting T1 maps. Simulation and phantom measurements predicted the expected increase in variability for Sh-MOLLI T1s to as much as 61%. However, in-vivo T1 measurements by Sh-MOLLI showed an increase in variability of only 14% (1.5 T) and 18% (3 T) as compared to MOLLI T1s. The repetition error was 16% for both methods at 1.5 T and only with excluding the worst measurements brought out the advantage of MOLLI at 3 T. For most of the T1 values tested, the in-vivo noise penalty for Sh-MOLLI due to a shorter imaging time is only 10-20%. While estimates of variability are inherently difficult to perform, we attribute this favorable observation to the likely beneficial effect of a 50% shorter breath-hold, resulting in fewer breathing artifacts and thus explaining the observed stability of Sh-MOLLI T1 maps in-vivo.

Overall, the use of a Sh-MOLLI sequence constitutes an excellent trade-off for significantly decreasing the imaging time and breath-hold, thereby making the Sh-MOLLI sequence much more clinically acceptable. Embodiments of the Sh-MOLLI sequence for myocardial T1-mapping generate robust, high resolution quantitative T1 maps in agreement with published data in a reduced number of heart beats across a wide range of heart rates and T1 values.

Significantly, single, short breath-holds are easily achievable for patients and therefore, the Sh-MOLLI technique permits wider clinical application of quantitative mapping. Implementation on non-linear T1 fitting directly in the scanner image reconstruction pipeline yields immediate access to T1-maps for viewing, allowing for re-acquisition if necessary. In patients presenting with acute myocardial infarction, preliminary data shows that Sh-MOLLI is able to distinguish injured from normal myocardium, with areas of long T1 co-localizing with injured myocardium as assessed by LGE. Due to demonstrated good measurement properties over wide range of T1 values Sh-MOLLI is a superior method for in-vivo contrast and non-contrast quantitative T1-mapping of myocardium or any other tissue where cardiac motion is of concern, particularly where short breath holds are required.

Figure 10:
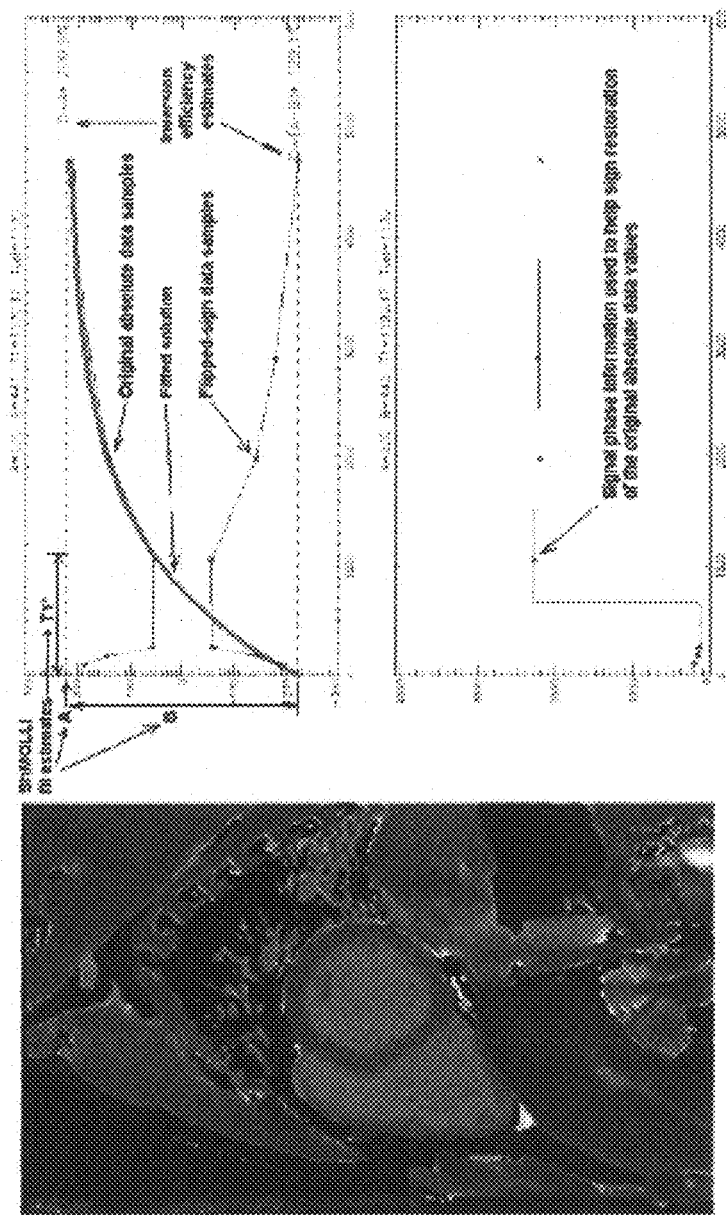
FIG. 10 illustrates reconstruction of the T1 recovery by brute force sampling of all or selected potential permutations between absolute and sign-inverted signal samples in any combination with the additional information from the measurements of signal phase.

FIG. 10 illustrates reconstruction of the T1 recovery value by brute force sampling of all or selected potential permutations between absolute and sign-inverted signal samples in any combination with the additional information from the measurements of signal phase. This improves the robustness and speed of the proposed reconstruction algorithm. The displayed parametric maps of the solution values for A, B, T1*, T1 and calculation step numbers, obtained at any stage of the Sh-MOLLI related reconstruction algorithm are shown, in addition to maps of any derivations based on such parameters, such as but not limited to, the efficiency of magnetization inversion estimates "D" shown in FIG. 10.

Figure 11:
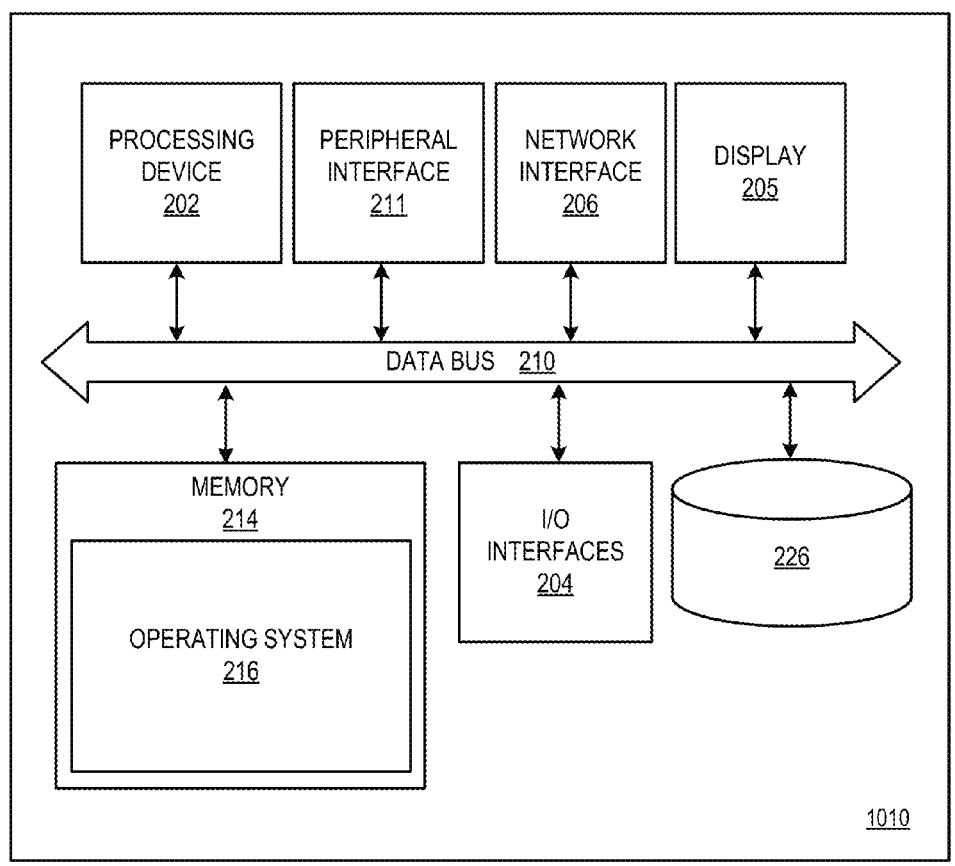
FIG. 11 is a schematic block diagram of an apparatus in which embodiments of the Sh-MOLLI technique may be implemented.

Reference is made to FIG. 11, which depicts an apparatus 1010 in which the Sh-MOLLI technique described herein may be implemented. The apparatus 1010 may be embodied in any one of a wide variety of wired and/or wireless computing devices, multiprocessor computing device, and so forth. As shown in FIG. 11, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the Sh-MOLLI technique described herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, or other display device.

In the context of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 11, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices 103a, 103b (FIG. 1) via the network interface 206 over the network 118 (FIG. 1). The apparatus 1010 may further comprise mass storage 226. The peripheral 211 interface supports various interfaces including, but not limited to IEEE-1394 High Performance Serial Bus (Firewire), USB, a serial connection, and a parallel connection.

The apparatus 1010 shown in FIG. 11 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate immediate T1 maps available for viewing immediately after image acquisition, thereby allowing re-acquisition on-the-spot if necessary. One example of an apparatus in which the Sh-MOLLI sequence may be implemented is described in U.S. Pat. Nos. 5,993,398 and No. 6,245,027, which are incorporated by reference as if fully set forth herein.

The flowchart of FIG. 3 shows an example of functionality that may be implemented in the apparatus 1010 of FIG. 11. If embodied in software, each block shown in FIG. 3 may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 11) in a computer system or other system. The machine code may be converted from the source code, etc. If embodied in hardware, each block may represent a circuit or a number of interconnected circuits to implement the specified logical function(s).

Although the flowchart of FIG. 3 shows a specific order of execution, it is understood that the order of execution may differ from that which is depicted. For example, the order of execution of two or more blocks may be scrambled relative to the order shown. Also, two or more blocks shown in succession in FIG. 3 may be executed concurrently or with partial concurrence. Further, in some embodiments, one or more of the blocks shown in FIG. 3 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

At least the following is claimed:

1. A computer implemented method for performing myocardial spin-lattice (T1) mapping, comprising:

a) activating a pulse sequence, by at least one computing device, to perform consecutive inversion-recovery (IR) experiments that include front-loaded sampling followed by one or more subsequent samples, the consecutive inversion-recovery (IR) experiments including a first experiment acquiring the front-loaded sampling followed by a recovery epoch and the recovery epoch followed by a second experiment acquiring the one or more subsequent samples, wherein the number of samples acquired from the first experiment exceeds the number of samples acquired from the second experiment and the interval for the recovery epoch is knowingly chosen or accepted to be shorter than considered necessary for full magnetization recovery before initiating the second experiment;

b) calculating an empirical relationship between an estimated spin-lattice relaxation time T1, a heart rate, a heart beat period, an experimentally achieved relaxation recovery time or degree, or an estimated fit error associated with the one or more subsequent samples, or two or more combinations thereof; and c) obtaining individual T1 estimates for the T1 mapping by using the calculated empirical relationship to determine whether to include the subsequent one or more samples for the T1 mapping.

2. The method of claim 1, further including the step of calculating whether the T1 time of the first experiment is shorter than a predefined interval.

3. The method of claim 2, wherein the predefined interval is based on a heart beat interval.

4. The method of claim 1, wherein the first experiment acquires a five sample data set.

5. The method of claim 1, wherein intervals for the recovery epoch and the second experiment are determined based on a number of heartbeats and the IR experiments are split over a predetermined number of heartbeats.

6. The method of claim 1, wherein the consecutive IR experiments comprise a second recovery epoch following the second experiment, and a third experiment following the second recovery epoch, the second and the third experiments acquiring the one or more subsequent samples, the first experiment acquiring a number of samples exceeding a number of samples of both the second experiment and the third experiment.

7. The method of claim 6, wherein the number of samples acquired in the first experiment is five.

8. The method of claim 7, wherein the number of samples acquired in the second experiment is one.

9. The method of claim 8, wherein the number of samples acquired in the third experiment is one.

10. The method of claim 6, further comprising calculating whether a fit error (FE) normalized by a number of samples in the first, second, and third experiments is less than a FE based on the samples in the first experiment.

11. The method of claim 6, wherein the first, second, and third experiments are split over a predetermined number of heartbeats.

12. The method of claim 6, wherein the interval for the second recovery epoch, comprised of data collection and unperturbed recovery epoch, is equal to or more than the interval for the third experiment.

13. The method of claim 1, wherein the step of calculating an empirical relationship includes:
determining an initial spin-lattice (T1) estimation; and
based on the initial T1 estimation, calculatinq whether a T1 value associated with the samples in the first experiment is less than a heart beat interval.

14. The method of claim 13, wherein the calculation of whether a T1 value associated with the samples acquired from the first experiment is less than a heat beat interval is performed only if the initial T1 estimation is greater than a predetermined threshold.

15. The method of claim 13, further comprising calculating whether a fit error (FE) normalized by a number of samples in both the first experiment and the second experiment is less than a FE based on the samples in the first experiment.

16. The method of claim 15, wherein the FE is calculated based on a square root of a sum of squared residuals divided by a number of samples minus one.

17. The method of claim 15, further comprising processing the samples in the second experiment if the fit error (FE) normalized by a number of samples in both the first experiment and the second experiment is calculated to be less than a FE calculated based on the samples in the first experiment.

18. The method of claim 1, further utilizing the samples acquired from the consecutive inversion-recovery (IR) experiments for non-linear T1 fitting based on T1 relaxation times.

19. The method of claim 18, wherein the one or more samples acquired from the second experiment are utilized if an estimated T1 is calculated to be shorter than a heart beat interval and if utilization of the one or more samples in the second experiment improves the non-linear fit.

20. The method of claim 1, wherein the step of calculating an empirical relationship calculates an empirical relationship based on an estimated spin-lattice relaxation time T1 and includes calculating whether T1 values are larger than a predetermined interval and if so then using only the samples acquired from the first experiment for the T1 mapping.

21. The method of claim 1, wherein the step of calculating an empirical relationship involves a calculation of fit errors associated with the one or more subsequent samples.

22. The method of claim 1, wherein the consecutive inversion-recovery (IR) experiments are carried out over intervals based on a heartbeat and the total number of heartbeats for all of the intervals is less than 12.

23. The method of claim 1, wherein the consecutive inversion-recovery (IR) experiments are carried out over intervals based on a heartbeat and the total number of heartbeats for all of the intervals is less than 10.

24. The method of claim 1, further comprising calculating a fit error (FE) normalized by a number of samples in both the first experiment and any subsequent one or more experiments and calculating whether the fit error (FE) is less than a FE based on the samples in one or more preceding experiments.

25. The method of claim 1, wherein the total number of samples in preceding experiments exceeds the number of samples from any subsequent experiment by at least two.

* * * * *